US 6,585,748 B1

(12) United States Patent
Jeffree

(10) Patent No.: US 6,585,748 B1
(45) Date of Patent: Jul. 1, 2003

(54) DEVICE FOR TREATING ANEURYSMS

(75) Inventor: Martin Andrew Jeffree, Orpington (GB)

(73) Assignee: King's Healthcare NHS Trust of King's College, London (GB)

( * ) Notice: Subject to any disclaimer, the term of this patent is extended or adjusted under 35 U.S.C. 154(b) by 0 days.

(21) Appl. No.: 09/463,069
(22) PCT Filed: Jul. 20, 1998
(86) PCT No.: PCT/GB98/02165
§ 371 (c)(1),
(2), (4) Date: Mar. 28, 2000
(87) PCT Pub. No.: WO99/03404
PCT Pub. Date: Jan. 28, 1999

(30) Foreign Application Priority Data

Jul. 18, 1997  (GB) .............................. 9715241

(51) Int. Cl.[7] .............................. A61M 29/00
(52) U.S. Cl. .................................... 606/200
(58) Field of Search ................. 606/200, 108, 606/127, 113, 114, 194, 195, 153; 623/1.1

(56) References Cited

U.S. PATENT DOCUMENTS

| 4,364,392 A | * | 12/1982 | Strother et al. | ........ | 604/103.01 |
| 4,638,803 A | * | 1/1987 | Rand | ............ | 604/175 |
| 5,041,090 A |   | 8/1991 | Scheglov et al. | | |
| 5,176,692 A | * | 1/1993 | Wilk et al. | ............ | 604/103 |
| 5,334,210 A |   | 8/1994 | Gianturco | | |
| 5,584,803 A | * | 12/1996 | Stevens et al. | ........ | 604/101.01 |
| 5,861,003 A | * | 1/1999 | Latson et al. | ............ | 606/157 |
| 5,928,260 A | * | 7/1999 | Chin et al. | .............. | 604/107 |
| 6,346,117 B1 | * | 2/2002 | Greenhalgh | ............. | 606/200 |

FOREIGN PATENT DOCUMENTS

| WO | WO 95/12367 | 5/1995 |
| WO | WO 96/01591 | 1/1996 |
| WO | WO 96/18343 | 6/1996 |
| WO | WO 97/26939 | 7/1997 |

* cited by examiner

Primary Examiner—Michael J. Milano
Assistant Examiner—(Jackie) Tan-Uyen T. Ho
(74) Attorney, Agent, or Firm—J. Charles Dougherty

(57) ABSTRACT

A device (30) for treating aneurysms comprises a bag (31) removably attached to the distal end of a catheter (14), the bag being arranged to be inserted in an aneurysm (20) and being of flexible and stretchable material and being permeable to blood components. Once the bag is inserted, individual GD coils (18) are introduced therein. The bag is inserted by a shoulder (42) or a widened portion (50) of a guide wire (40) engaging a marker ring (46). The bag material may encourage clotting. In another embodiment the bag (131) is located around the end of the catheter (114) during insertion. When insertion is completed, electrolysable struts (32, 172) are removed to separate the bag from the catheter.

18 Claims, 3 Drawing Sheets

DEVICE FOR TREATING ANEURYSMS

The present invention relates to a device for treating aneurysms and in particular to a device for use in the endovascular treatment of intracranial aneurysms.

Two earlier patent documents disclose similar devices but, because they concern devices for blocking vessels within the patient, are not designed for occluding aneurysms. In particular, U.S. Pat. No. 5,334,210 discloses a vascular occlusion assembly which comprises a bag made of rip stop nylon material so as to prevent the passage of blood. The bag has a predetermined diamond shape and thus would not be suitable for conforming to aneurysms. Moreover, the heavy and non-stretch nature of the material of the bag would make it difficult to steer through fine intracranial blood vessels. No guide wire is provided and the bag is attached and detached by a frictional arrangement.

Similarly, WO96/01591 also discloses a self-expanding vascular occlusion device. A pre-moulded basket of metal fabric is collapsed for passage through a catheter, placed in location by a guide wire affixed to the basket, and subsequently expanded within a channel in a patient's body. Since the passage of a metallic body is traumatic to patients, the basket moves along the interior of the catheter.

Devices in accordance with the present invention are especially suitable for use with a Guglielmi Detachable Coil arrangement (GD coil as disclosed in Gugleilmi G., Vinuela F., Duckwiler G., Dion J., et al. Endovascular treatment of posterior circulation aneurysms using electrically detachable coils. J Neurosurgery. 77: 515–524, 1992.

Saccular intracranial (cerebral) aneurysms occur when regions of weakness in the wall of intracranial arteries result in the development of balloon-like swellings on the sides of the arteries. They are important because they are prone to burst and cause haemorrhage over the surface of the brain (subarachnoid haemorrhage). This can result in death in over 30% of patients within 24 hours and a further 25–30% will die within the next four weeks without some form of surgical intervention.

Until recently the conventional treatment of cerebral aneurysms was to perform a neuro-surgical operation to place a clip across the neck of the aneurysm, analogous to tying the neck of a balloon. Over the past 10 to 15 years, endovascular techniques of aneurysm occlusion have evolved. The common principle to these techniques is that devices or materials are delivered by a tube (catheter) through the parent artery into the aneursym where they induce clotting of the blood (thrombosis) in the aneurysm and effectively remove it from the circulation. The catheter is generally inserted via the femoral artery in the groin and the procedure monitored by x-ray flurosocopy. The devices therefore have to be manipulable remotely, at a distance of approximately one meter without the help of direct vision. In the mid 1980s, balloons were used, made of latex or silicone rubber, to occlude the aneurysm. The results were poor and the mortality high. The reasons for this were: 1. It is rare that an aneurysm can be perfectly filled with one balloon. 2. If more than one balloon is used, large unfilled spaces must remain in the aneurysm (one sphere cannot be perfectly filled with more than one smaller spheres). 3. Distension of the aneurysm will be the balloon(s) is likely to occur and cannot be seen or measured.

Other workers had greater success using sort coils of inert metal, generally platinum, to pack the aneurysm and induce thrombosis within it. The first coils were 'free' in that they were simply pushed up the catheter into the aneurysm and once out of the catheter they could not be retrieved. This made the procedure difficult to control and hence risky.

In 1991 a major advance in coil technology, the GD coil, was developed and it remains the only accepted device used in the endovascular treatment of cerebral aneurysms. Although essentially simply a soft platinum coil, it differs from the "free" coils in that it is captive and therefore controllable until the user chooses to release it.

The GD coil has proved very successful especially for aneurysms of the posterior intracranial circulation. It is often used in the treatment of aneurysms which are thought to be inoperable by other means.

The GD coil is not without problems, however, and amongst these are:
1. Relatively poor results in large (>1 cm diameter) or giant (>2 cm diameter) aneurysms, generally because of a tendency for the coil mass to pack down and for the neck region of the aneurysm to enlarge with time after treatment.
2. Failure of endothelium to grow across the neck of treated aneurysms.
3. Tendency for coils to prolapse out of wide necked aneurysms and obstruct the parent artery.
4. Early (procedural) or delayed (post treatment) rupture of the coils through the aneurysm wall.

The present invention seeks to overcome, or reduce, one or more of the above problems.

WO-A-96/18343 discloses an arrangement with an embolic coil having its own surrounding net. EP-A-0352325 discloses an arrangement comprising inner and outer balloons, either of which may be perforated. WO-A-96/12367 discloses an embolic device in which detachment is achieved by means of a sacrificial link which is susceptible to electrolytic disintegration.

According to a first aspect of the present invention there is provided an arrangement for treating aneurysms comprising a catheter, a bag removably attached to one end of the catheter and with its interior in communication with the catheter, the bag being arranged to be inserted in an aneurysm, and at least one insert characterised in that means are provided for placing the or each insert in the bag with the bag inside the aneurysm and before the bag is disconnected from the catheter.

The bag may be provided with a guide wire to assist insertion of the bag and the catheter. The bag may also comprise one or more marker rings, and the guide wire may have a shoulder which engages one of the rings in the manner of a one-way drive. Thus the guide wire may comprise first, narrow end portion on the end of a second portion in the form of a shaft, the portions defining a step or shoulder therebetween. Alternatively, the second portion may be constituted by a widened section of short extent, e.g. a ball-shaped member on a guide wire of otherwise uniform thinner cross-section.

The material of the bag is preferably flexible and stretchable in the manner of nylon stockings so that it can conform to the interior size and shape of the aneurysm. The material is non-metallic and may be made from natural or synthetic fibre material.

The material of the bag may be such as to encourage clotting or, alternatively, to discourage clotting.

The bag may be provided as part of a kit of parts including a bag, a catheter to which the bag is removably attached, and a guide wire.

According to a second aspect of the present invention there is provided a device for introducing an annular or part-annular member into a patient, comprising a catheter having an element at or adjacent one end thereof, with at least one electrode extending along the catheter to said element, characterised in that said element is connected to said member by two or more spaced struts, the struts being arranged to be removed electrolytically when an electric current is passed through said electrode.

The element on the catheter is preferably also annular or part-annular so that the struts provide a stable arrangement for maintaining the member and the element relatively fixed, e.g. with their planes substantially parallel.

Preferred embodiments of the present invention will now be described, by way of example only, with reference to the accompanying drawings, of which:

Figure 1:
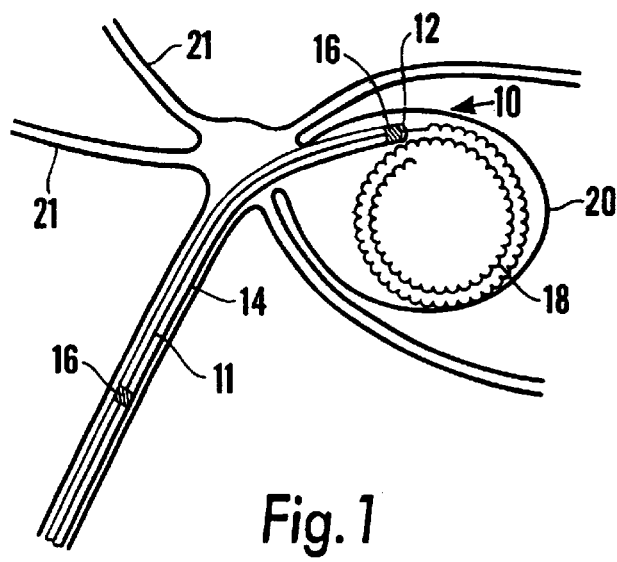
FIG. 1 is a sectional view of a conventional GD coil inside an intra-cranial aneurysm.
Figure 2:
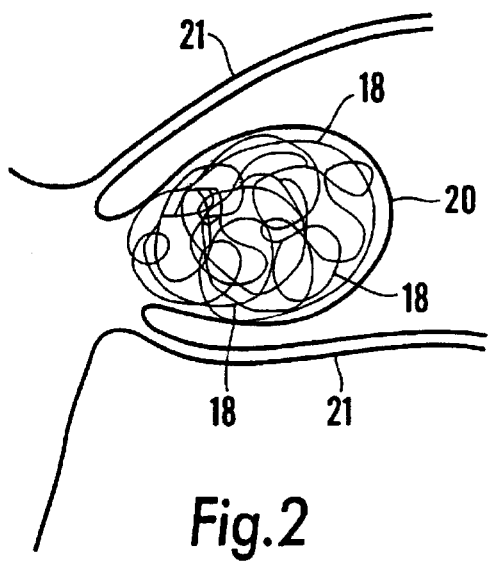
FIG. 2 is a view of the aneurysm of FIG. 1 after it has been packed with GD coils.

When using the GD coils alone, according to the prior art and shown in FIGS. 1 and 2, each device 10 comprises a coil 18, welded or soldered by means of a single connection on to a pushing steel wire 11 which is very thin just proximal to a solder joint 12. The wire is electrically insulated up to a point approximately 1 mm from the joint 12. The device 10 is introduced into the aneurysm 20 via a catheter 14. Normal cranial arteries are indicated at 21. Platinum markers 16 on the catheter 14 and the pushing wire 11, when aligned, indicate that the coil 18 is in an ideal position for detachment.

Once the device 10 has been manipulated into an ideal position, a small positive voltage (approximately 3.5 V) is applied to the proximal end of the wire. The negative terminal is attached to an earthing needle in the pateint's groin. A current of 1 mA passes which causes electrolytic erosion of the distal end of the pushing wire and detachment of the coil 18 in approximately 2 minutes. Further coils 18 are inserted in sequence until the aneurysm is well packed and it becomes difficult to insert any more, see FIG. 2.

Figure 3:
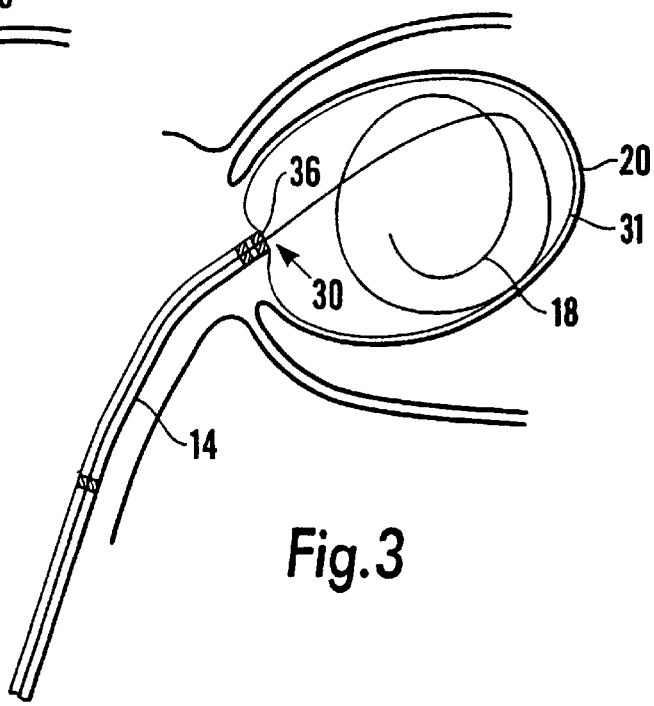
FIG. 3 is a view of a device in accordance with a first embodiment of the present invention inside an intra-cranial aneurysm.
Figure 4:
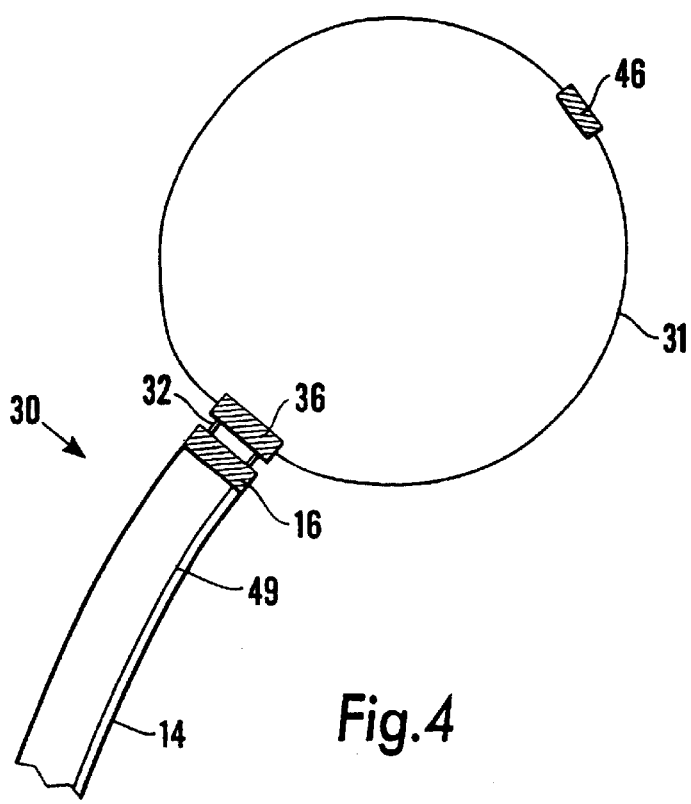
FIG. 4 is an enlarged view of the device of FIG. 3.
Figure 5:
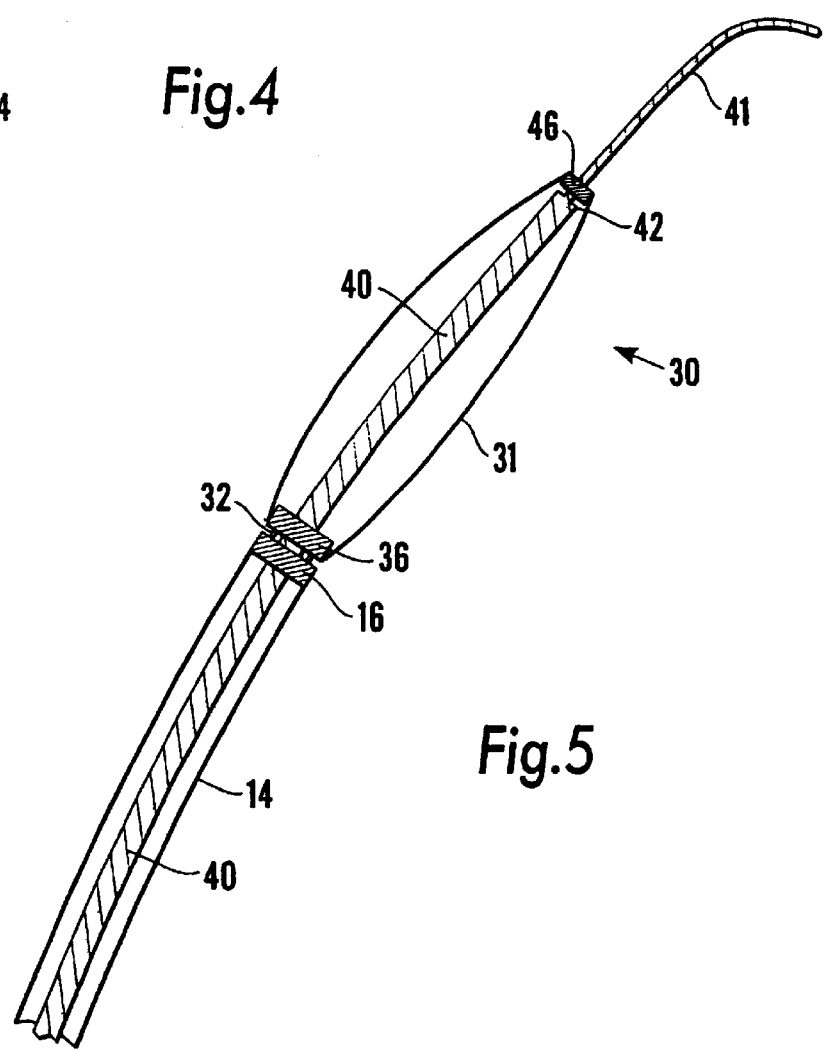
FIG. 5 is a similarly enlarged view of the device of FIGS. 3 and 4, but in a collapsed state for insertion.

FIGS. 3 to 5 show a device 30 in accordance with the present invention comprising a bag or envelope 31 forming a linear and removably attached by means of two steel detachment struts 32 to the distal end of a catheter 14.

The basis concept of this embodiment is to insert the bag 31 into the aneurysm 20 before inserting the GD coils.

Briefly, the bag 31 is an approximately spherical envelope of material which is porous to liquids, including blood. It is provided in a range of sizes which can be matched to the aneurysm 20. It is inserted into the aneurysm 20 on the end of the catheter 14 and remains attached to the catheter while GD coils 18 (or other materials) are inserted into it, thus expanding it against the walls of the aneurysm. When the coil mass is complete and detached, the bag 31 is detached from its delivery catheter 14 and the catheter withdrawn.

A guide wire 40, FIG. 5 normally employed to insert just a catheter, is here used to direct the bag 31 at the end of catheter 14 to the size of the aneurysm 20. The guide wire has a tip 41 of narrow cross-section forming a shoulder 42 with the remainder of the wire. Tip 41 may have a length of approximately 1 to 2 cm and is more flexible than the remainder of the wire to assist insertion. The wire cross-sections are such that wire 40 can pass freely through a platinum base (or sound-polar) marker ring 36 of bag 31, but only tip 41 can pass through a platinum apical (or north-polar) marker ring 46. Thus by virtue of shoulder 42 engaging the apical marker 46, the guide wire operates as a one-way drive for inserting the bag 31 and the attached catheter 14. Insertion is facilitated by the wider part of wire 40 keeping the bag stretched longitudinally and thus stretching the bag into a relatively long narrow configuration. This facilitates navigation in the blood vessels and guidance into the aneurysm.

Alignment of bag base marker 36 and catheter marker 16 is used to ensure correct location of the bag 31. When the bag is correctly positioned, the guide wire 40 is withdrawn leaving the bag attached to the catheter 14.

GD coils 18 attached to respective pusher wires 11 are then introduced sequentially along catheter 14 and inserted in the bag 31 as in the previously-known method.

The bag then expands to conform to the interior of the aneurysm as shown in FIG. 3. When the bag 31 is packed to a satisfactory amount and the last GD coil 18 has been detached and its pusher wire 11 removed the bag 31 is then detached from the catheter 14. The catheter detachment mechanism is a modification of the GD coil attachment, and electrolytic detachment is possible. The bag has attached to its base a small ring (not shown) of platinum or other suitable material, and of the same or similar diameter as the catheter. This ring is mounted on top of the distal marker ring 16 of the delivery catheter and is attached to it by the two thin steel struts 32. The distal marker ring 16 is in turn connected to a fine electrode 49 embedded in the wall of the delivery catheter. Detachment is by electrolysis of the steel struts 32 in much the same way as a GD coil is detached.

The material of the bag 32 is a very fine knitted, braided or woven fabric allowing some degree of local stretch. The bag is as non-bulky as possible in its collapsed state to pass through the guide catheter and blood vessels, but has to be able to expand to the size of the aneurysm, possibly up to 3 cm diameter, without significant resistance until it reaches its design size. A range of sizes will be made for different aneurysms, its knit, braid or weave is dense enough to resist penetration by the top of a coil 18. A preferred material is 5-denier nylon. The bag is strong enough to contain the coils 18 and prevent them prolapsing out of the neck of the aneurysm 20. Thus the entire bag 31 is arranged to be located within the aneurysm, leaving the blood vessels 21 completely clear.

The use of the bag 31 strengthens the aneursym walls to reduce the risk of aneurysm rupture, bridges its neck and contains the coils, facilitating insertion of the coils 18 and reducing the chance of coil prolapse. Also, the bag 31 is of stretchy material and is not self-expanding; although it is of approximately spherical shape, it conforms to the shape of the particular aneursym, particularly upon the insertion of coils 18. Further, the bag induces fibrosis in the aneurysm walls, strengthening them permanently and also forms a framework for endothelial cells to grow across the neck of the aneurysm, thus restoring normal blood flow in the parent artery. It allows better treatment of giant aneurysms and reduces the likelihood of regrowth of the aneurysm.

Figure 6:
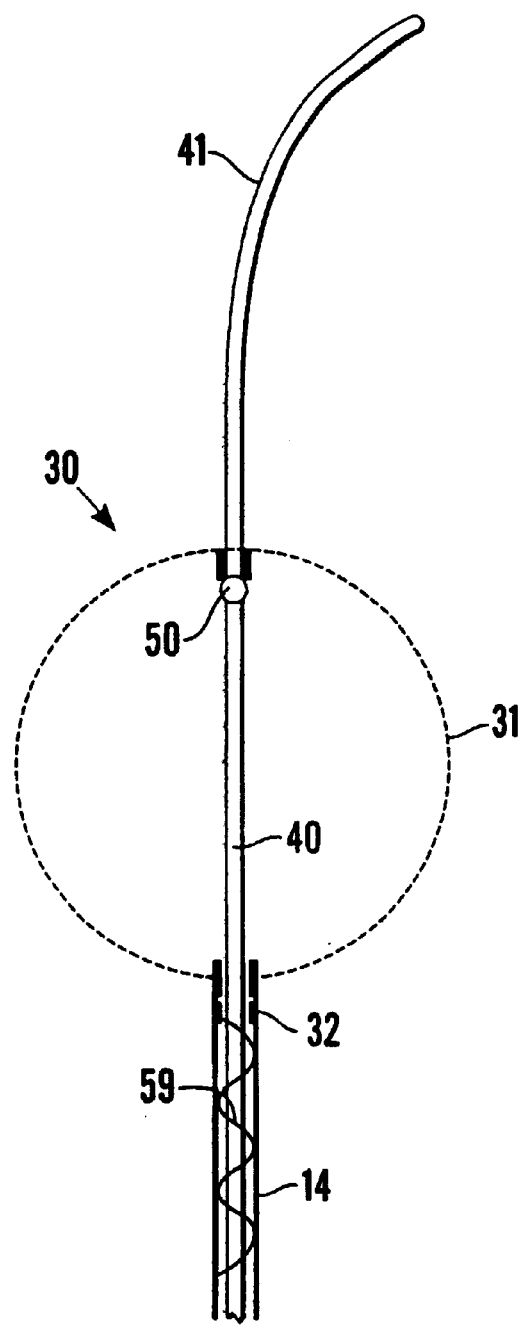
FIG. 6 shows a modified device in accordance with the present invention.

Various modifications may be made to the above-described device. For example, as shown in the modification of FIG. 6, the guide wire 40 can have a short region 50 of increased width, e.g. of the type known as a "ball". This is provided between the lip 41 and the shaft of the guide wire. In this case the microcatheter 14 has a helical electrode 59 embedded in its wall for electrolysing the struts 32.

Alternatively, the way in which the device 30 is inserted may be changed and the marker rings 36, 46 may be of the same diameter or the end of the catheter 14 may be arranged to pass through the base marker 36 but not the apex marker 46.

The references to rings include rings of any shape and also to part-rings.

Any number of struts 32 may be provided including one, or three or more. Alternatively, mechanical attachment and detachment devices might be employed or a frictional attachment followed by detachment by pulling the catheter 14 out or pushing off the bag 31.

The material of the bag 31 may be a very fine version of the types of material used to make tights. Natural fibers such as silk, or man-made fibers such as nylon, Lycra, Dacron or Teflon may be appropriate. Porous membranes such as Gore-Tex may be considered. (Gore-Tex is conventionally thought of as impermeable to water-based liquids; however if it is pre-wetted with alcohol and the alcohol is then replaced with water, water will pass freely through it. Plasma will also pass through it though the cellular elements of blood will not). Although the chosen material may act as a framework for the invasion by fibroblasts or endothelial cells, it is possible to impregnate the fabric with other materials, e.g. collagen, to stimulate cell growth or heparin to reduce its thrombogenicity. (Lycra, Dacron, Teflon and Gore-Tex are registered trade marks).

In a modification, the bag may be in the form of a balloon, e.g. of Dacron sheet material having a plurality of perforations. This has the advantages of being strong, smooth and lightweight and complex. However, it may not be sufficiently elastic to conform to the shape of a particular aneurysm.

Electrodes 49, 59 can be of braided conductive material embedded in the catheter wall.

Figure 7:
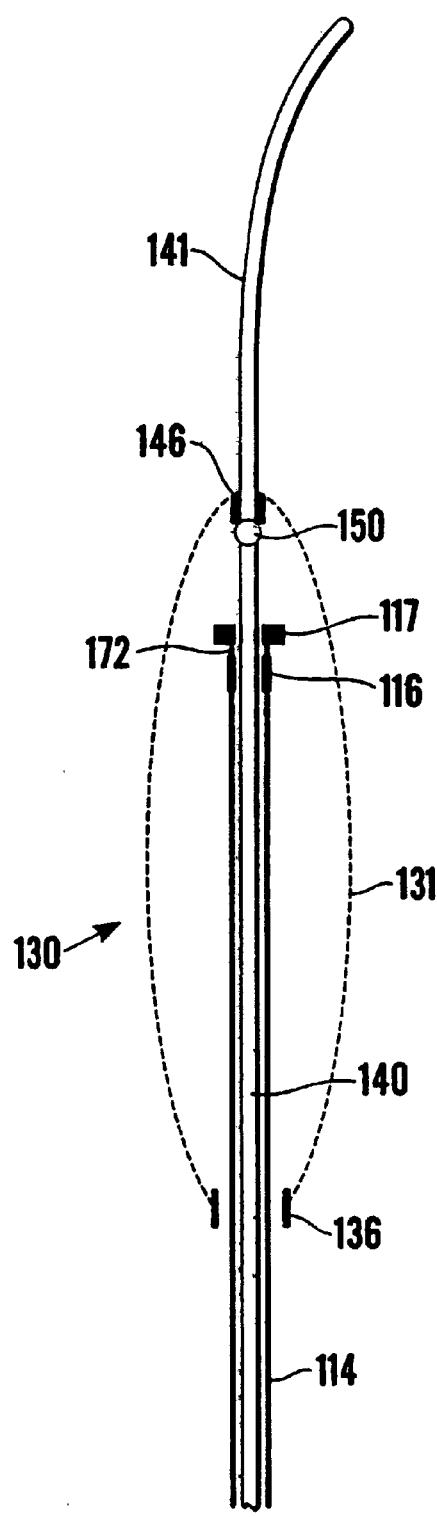
FIG. 7 shows a device in accordance with a second embodiment of the present invention.

In the embodiment of FIG. 7, a device 130 has a microcatheter 114 which together with its marker ring 116 can actually pass through the south-polar ring 136 of the linear bag 131. The ring 136 is free to move to and fro along the distal end region of the catheter 14. A detachable ring 117, which is too wide to pass through south-polar ring 136, is attached to catheter marker ring by two electrolysable struts 172. Ball 150 of the guide wire 140 is too broad to pass through the north-polar ring 146, but sufficiently narrow to pass through the detachable ring 117, the terminal marker 116 and the catheter 114. Again guide wire 140 has a relatively flexible tip 141. Also, catheter 114 has an electrode (not shown) embedded in its walls for removing struts 172 when desired.

In use, the device 130 is assembled with ring 117 inside bag 131 so that the bag 131 is loosely retained on the distal end of the catheter. The device is steered into the aneurysm with the bag 131, the catheter 114 and the guide wire 140 in approximately the relative positions shown, although the catheter could be advanced slightly relative to the bag. The detachable ring 117 can be pushed right up against the north-polar ring 146 of the bag.

The guide wire 140 is then withdrawn from the catheter, and the catheter is retracted slightly so that its distal end lies near the centre of the bag. Coils 18 can then be deployed through the catheter and into the bag inside the aneurysm. As the bag 131 is filled, the catheter can be urged towards the south-polar ring 136, but ring 117 prevents the catheter from leaving the bag.

When the bag has been filled, the struts 172 are electrolysed away so that ring 117 is detached. Catheter 114 is then withdrawn from bag 131 and removed from the patient. The south-polar ring 136 ensures that ring 117 is remained inside the bag with the coils 18; accordingly, ring 117 should be made of an appropriate material.

An advantage of this embodiment is that it is more easily steerable towards and into the aneurysm. Also, it permits a more accurate control of the position of the release of the coils 18 within the bag 131.

The bags 31, 131 may be filled with elements other than GD coils, e.g. elements of different shapes and/or elements which contain or include a material which can initiate a healing response. The inserts could include detachable or pushable platinum coils, injectable particles or materials which are injected as a liquid but which solidify in the bag. These materials may or may not include a bio-active material to induce a healing response.

Indeed, if the bags 31, 131 are made of a suitable material with a suitable porosity, there may be no need to fill them with elements 18 and it may be enough to cause the bags to inflate within the aneursym. Also, the bags may be impermeable to all components of blood.

The above-described devices can also be used with aneurysms located elsewhere in the body.

In conclusion, a summary of some of the properties that the preferred bags exhibit is as follows:

1. Small enough, in the collapsed state, to pass through existing guide catheter systems.
2. Flexible enough to negotiate tortuous blood vessels.
3. Steerable by a guide wire.
4. Expandable to its design size by GD coils.
5. Strong enough to contain the coils and strengthen the aneurysm.
6. Non-toxic.
7. Have radio-opaque markers so that its position can be monitored.
8. Securely attached to delivery catheter but detachable when necessary.
9. Allow invasion by and act as a framework for fibroblasts and endothelial cells.
10. Stretchable between longitudinal and approximately spherical configurations.

I claim:

1. An arrangement for treating aneurysms comprising a catheter, a bag removably attached to one end of said catheter, the interior of the bag being in communication with said catheter and the bag being arranged to be inserted in an aneurysm, and a plurality of inserts wherein insert-placing means are provided for placing each insert in the bag with the bag inside the aneurysm and before the bag is disconnected from said catheter wherein the bag is of a material which is permeable to at least some of the components of the blood.

2. An arrangement according to claim 1, wherein the bag is of a flexible and stretchable material.

3. An arrangement according to claim 1, wherein said insert-placing means comprise a respective pusher wire for each insert.

4. An arrangement according to claim 1, wherein the material of the bag encourages a healing response.

5. An arrangement according to claim 1, wherein the bag is of a knitted material.

6. An arrangement according to claim 1, wherein the bag is of a woven material.

7. An arrangement according to claim 1, wherein the bag is of a braided material.

8. A device for introducing an at least partially annular member into a patient, comprising a catheter having an element adjacent one end thereof, with at least one electrode extending along said catheter to said element, wherein said element is connected to said member by a plurality of spaced struts, said struts being arranged to be removed electrolytically when an electric current is passed through said electrode.

9. An arrangement for introducing a bag into a patient and comprising a guide wire and said bag, wherein said bag includes a substantially annular opening and said guide wire is provided with a first portion, said first portion passing freely through said opening and a second portion, said second portion not passing through said opening, whereby said guide wire constitutes a one-way drive means for introduction of said bag.

10. An arrangement for treating aneurysms comprising a catheter, a bag removably attached to one end of said catheter, the interior of the bag being in communication with said catheter and the bag being arranged to be inserted in an aneurysm, and at least one insert wherein insert-placing means are provided for placing each insert in the bag with the bag inside the aneurysm and before the bag is disconnected from said catheter, wherein the bag has at least one marker ring and a guide wire with a widened section, said widened section engaging said marker ring in the manner of a one-way drive.

11. An arrangement for treating aneurysms comprising a catheter, a bag removably attached to one end of said catheter, the interior of the bag being in communication with said catheter and the bag being arranged to be inserted in an aneurysm, and at least one insert wherein insert-placing means are provided for placing each insert in the bag with the bag inside the aneurysm and before the bag is disconnected from said catheter, wherein the bag comprises an at least partially annular member and said catheter has an element adjacent one end thereof, at least one electrode extending along said catheter to said element, said element being connected to said member by a plurality of spaced struts, said struts being capable of being removed electrolytically when an electric current is passed through said electrode.

12. An arrangement according to claim 11, wherein said element on the catheter is annular, said struts being arranged to maintain the planes of said member and said element substantially parallel.

13. An arrangement for treating aneurysms comprising a catheter, a bag removably attached to one end of said catheter, the interior of the bag being in communication with said catheter and the bag being arranged to be inserted in an aneurysm, and a plurality of inserts wherein insert-placing means are provided for placing each insert in the bag with the bag inside the aneurysm and before the bag is disconnected from said catheter.

14. An arrangement according to claim 13, wherein the bag is of a flexible and stretchable material.

15. An arrangement according to claim 13, wherein said insert-placing means comprise a respective pusher wire for each said insert element.

16. An arrangement according to claim 13, wherein the material of the bag encourages a healing response.

17. An arrangement according to claim 13, wherein the bag is of a material which is permeable to at least some of the components of the blood.

18. A method of treating an aneurysm comprising the steps of:

(a) introducing a bag into the aneurysm, said bag being removably attached to one end of a catheter, the interior of said bag in communication with said catheter;

(b) sequentially introducing a plurality of insert elements along said catheter and into said bag;

(c) disconnecting said bag from said catheter, leaving said bag in the aneurysm; and (d) removing said catheter.

* * * * *